Figure 1:
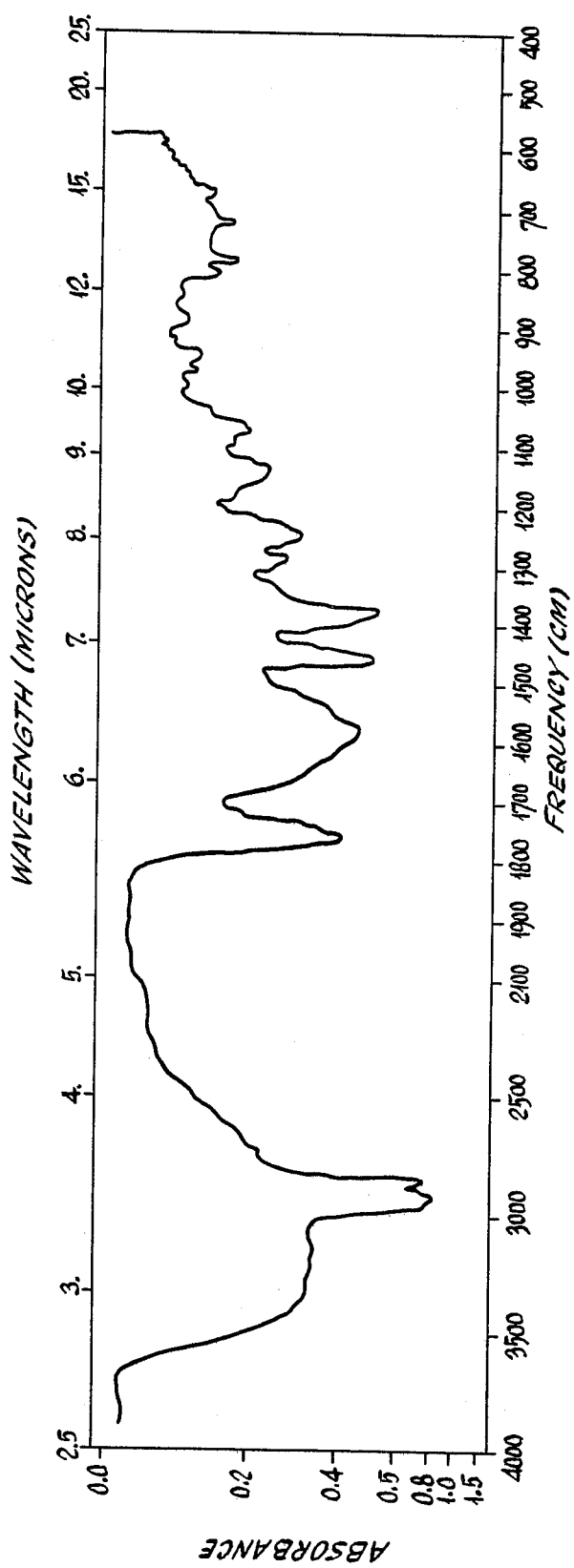

United States Patent [19]

Kahan et al.

[11] 4,081,548

[45] Mar. 28, 1978

[54] ANTIBIOTICS

[75] Inventors: Jean S. Kahan; Frederick M. Kahan, both of Rahway; Edward O. Stapley, Metuchen; Robert T. Goegelman, Linden, all of N.J.; Sebastian Hernandez, Madrid, Spain

[73] Assignee: Merck & Co., Inc., Rahway, N.J.

[21] Appl. No.: 720,483

[22] Filed: Sep. 3, 1976

Related U.S. Application Data

[62] Division of Ser. No. 632,938, Nov. 18, 1975, Pat. No. 4,006,060, which is a division of Ser. No. 526,992, Nov. 25, 1974, Pat. No. 3,950,357.

[51] Int. Cl.$^2$ ............................................. A61K 31/40
[52] U.S. Cl. ..................................................... 424/274
[58] Field of Search ........................................ 424/274

[56] References Cited
PUBLICATIONS

Hatanaka et al., J.C.S. Chem. Comm. p. 1364, (1971).

*Primary Examiner*—Jerome D. Goldberg
*Attorney, Agent, or Firm*—Richard A. Thompson; Julian S. Levitt

[57] ABSTRACT

The antibiotic thienamycin is active against both gram-positive and gram-negative bacteria. The antibiotic is produced by growing a newly-found and hitherto undescribed species of Streptomyces on suitable fermentation media.

1 Claim, 1 Drawing Figure

ANTIBIOTICS

This application is a divisional of U.S. Pat. Ser. No. 632,938, filed Nov. 18, 1975 now U.S. Pat. No. 4,006,060 which in turn is a divisional of U.S. Pat. Ser. No. 526,992, filed Nov. 25, 1974 which is now U.S. Pat. No. 3,950,357.

BACKGROUND OF THE INVENTION

The discovery of the remarkable antibiotic properties of penicillin stimulated great interest in this field which has resulted in the finding of many other valuable antibiotic substances such as: other penicillins, streptomycin, bacitracin, tetracyclines, chloramphenicol, erythromycins and the like. In general the antibacterial activity of each of these antibiotics does not include certain clinically important pathogenic bacteria. For example, some are principally active against only gram-positive types of bacteria. Acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

SUMMARY OF THE INVENTION

This invention relates to a new antibiotic agent. More particularly, it is concerned with a new antibiotic substance, herein called thienamycin. The invention encompasses the antibiotic in dilute forms, as crude concentrates and in pure forms.

It is an object of the present invention to provide a new and useful antibiotic which is highly effective in inhibiting the growth of various gram-negative and gram-positive microorganisms. Another object is to provide a process for the preparation of this novel antibiotic substance by the fermentation of nutrient media with a heretofore undescribed microorganism. Other objects will be apparent from the detailed description of this invention hereinafter provided.

The novel antibiotic substance of the present invention is produced by growing under controlled conditions the previously undescribed microorganism *Streptomyces cattleya*.

Based upon extensive taxonomic studies, *Streptomyces cattleya*, isolated from a soil sample, was identified as a hitherto undescribed actinomycete and has been designated MA-4297 in the culture collection of MERCK & CO., Inc., Rahway, N.J. A culture thereof has been placed on permanent deposit with the culture collection of the Northern Regional Research Laboratories, Northern Utilization Research and Development Division, Agricultural Research Service, U.S. Department of Agriculture, Peoria, Ill., and has been assigned accession No. NRRL 8057.

The classification keys for the genus *Streptomyces* and the culture descriptions of *Streptomyces* species found in Bergey's *Manual of Determinative Bacteriology* (7th Edition, 1957) and in *The Actinomycetes*, Vol. II (1961) by S. A. Waksman and in "Cooperative Descriptions of Type Cultures of *Streptomyces*" by E. B. Shirling and D. Gottlieb, *International Journal of Systematic Bacteriology*, 18, 69–189 (1968), 18, 279–392 (1968), 19, 391–512 (1969) and 22, 265–394 (1972) were searched for a *Streptomyces* species having morphological and cultural characteristics similar to those of MA-4297. In these aforementioned classical references, no *Streptomyces* species is described to have the orchid pigmentation of the aerial mycelium, the morphological characteristics and the absence of diffusible pigment which together comprise distinctive characteristics of MA-4297. These considerations make the assignment of a new *Streptomyces* species justified and necessary.

The morphological and cultural characteristics of *Streptomyces cattleya* are set forth in the following table. Morphology - Sporophores are compact spirals occurring as side and terminal branches on aerial mycelium. Spores are ellipsoidal to cylindrical in shape, $0.9\mu \times 1.2\mu$ in size, occurring in chains of more than 10.

CULTURAL

Tomato paste-oatmeal agar
    Vegetative growth - Reverse-tan, flat, spreading;
    Aerial mycelium - Orchid (10 gc) mixed with white;
    Soluble pigment - None.
Czapek Dox agar (sucrose nitrate agar)
    Vegetative growth - Colorless, flat, spreading;
    Aerial mycelium - Sparse, pinkish white;
    Soluble pigment - None.
Egg albumin agar
    Vegetative growth - Tan with grayed-orchid cast, flat, spreading;
    Aerial mycelium - Orchid (10 gc) mixed with lighter shades of orchid and some white;
    Soluble pigment - None.
Glycerol asparagine agar
    Vegetative growth - Reverse-tan with gray-pink cast, flat, spreading;
    Aerial mycelium - Orchid (10 gc) mixed with some white;
    Soluble pigment - None.
Yeast extract-glucose + salts agar
    Vegetative growth - Tan with grayed pink cast;
    Aerial mycelium - Orchid (10 gc) mixed with pinkish-white;
    Soluble pigment - None.
Yeast extract-malt extract agar
    Vegetative growth - Tan;
    Aerial mycelium - Orchid (10 gc) mixed with pinkish-white;
    Soluble pigment - None.
Peptone-iron-yeast extract agar
    Vegetative growth - Tan;
    Aerial mycelium - None;
    Soluble pigment - Slight browning of medium;
    Melanin - Negative;
    $H_2S$ production - Negative.
Nutrient agar
    Vegetative growth - Light tan;
    Aerial mycelium - None;
    Soluble pigment - None.
Nutrient starch agar
    Vegetative growth - Cream to tan;
    Aerial mycelium - None;
    Soluble pigement - None;
    Hydrolysis of starch - Moderate.
Nutrient gelatin agar
    Vegetative growth - Cream-colored;
    Aerial mycelium - None;
    Soluble pigment - None;
    Liquefaction of gelatin - moderate.
Gelatin stabs Vegetative growth - Tan;
Aerial mycelium - None;
Soluble pigment - None;
Liquefaction of gelatin - Moderate.

Potato plug
Vegetative growth - Moderate, tan;
Aerial mycelium - Sparse, grayish-pinkish-white;
Soluble pigment - None.

Loeffler's Blood serum
Vegetative growth - Cream-colored;
Aerial mycelium - None;
Soluble pigment - None;
Liquefaction - None.

Skim milk agar
Vegetative growth - Tan;
Aerial mycelium - Sparse, whitish;
Soluble pigment - Slight browning of medium;
Hydrolysis of casein - Positive.

Litmus milk
Vegetative growth - Tan to brown;
Aerial mycelium - None;
Color - No soluble pigment, litmus indicator becoming bluish;
Coagulation and/or peptonization - Partial peptonization, becoming alkaline.

Skim milk
Vegetative growth - Tan;
Aerial mycelium - None;
Soluble pigment - None;
Coagulation and/or peptonization - Partial peptonization, becoming alkaline.

Tyrosine agar
Vegetative growth - Tan;
Aerial mycelium - Mixture of orchid (10 gc) and white;
Soluble pigment - None;
Decomposition of tyrosine - positive.

All of the readings reported above were taken after three weeks incubation at 28° C. unless noted otherwise. The pH of the media used in these studies was approximately neutral, namely, pH 6.8 – 7.2. The color designations used in the description are in accordance with the definitions of the *Color Harmony Manual*, 4th Edition (1958), Container Corporation of America, Chicago, Illinois.

*Streptomyces cattleya* was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8 – 7.2). Table I shows the utilization of these carbohydrate sources by *Streptomyces cattleya:* + indicating good growth, ± poor growth, and − no growth on the particular carbohydrate.

TABLE I

| Glucose | + | Maltose | ± |
|---|---|---|---|
| Arabinose | − | Mannitol | + |
| Cellulose | − | Mannose | ± |
| Fructose | ± | Raffinose | − |
| Inositol | − | Rhamnose | − |
| Lactose | − | Sucrose | ± |
| Xylose | ± | | |

The amount of growth with change in temperature, the oxygen requirement and the effect on nitrate by the microorganism is as follows: Temperature range (Yeast extract-glucose + salts agar);

28° C - Good
37° C - Moderate
50° C - No growth

Oxygen requirement (Stab culture in yeast extract-glucose + salts agar);
Aerobic
Nitrate reduction - Positive.

It is to be understood that for the production of new antibiotics of this invention, the present invention is not limited to the organism *Streptomyces cattleya* or to organisms fully answering the above growth and microscopic characteristics which are given for illustrative purposes. In fact, it is desired and intended to include the use of mutants produced from the described organism by various means, such as X-radiation, ultraviolet radiation, nitrogen mustard, phage exposure and the like.

The novel antibiotic of the invention, thienamycin, is produced during the aerobic fermentation of suitable aqueous nutrient media under controlled conditions via the inoculation with the organism, *Streptomyces cattleya*. Aqueous media, such as those employed for the production of other antibiotics are suitable for producing thienamycin. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, rye, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 22° C. to 30° C. The pH of the nutrient media suitable for growing the *Streptomyces cattleya* culture and producing thienyamycin can vary from about 6.0 to 8.0.

Although the novel antibiotic thienamycin is produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 24° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for two days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 24° C. This method of producing thienamycin is particularly suited for the preparation of large quantities of the antibiotic.

PHYSICAL AND CHEMICAL PROPERTIES OF THIENAMYCIN

Thienamycin is a white solid which is very soluble in water, and has a limited solubility in methanol.

The apparent molecular weight in phosphate-buffered solutions is calculated to be about 282 Daltons, as determined by analytical ultracentrifugation, using short column sedimentation technique and ultraviolet absorption optics to monitor the sedimentation boundary of materials absorbing at 300 nm. Field-desorption mass spectrometry indicates a molecular weight of 272. From an energy dispersive analysis of X-rays emitted by the antibiotic under the beam of a scanning electron microscope, a combining molecular weight of 290±20 was established based on sulfur, that being the sole element, of atomic number greater than 9, found present in significant proportions.

Thienamycin has the empirical formula $C_{11}H_{16}N_2O_4S$ as deduced from high resolution mass spectrometry. The calculated elemental composition corresponding to this empirical formula is: 48.52% carbon, 5.92% hydrogen, 10.29% nitrogen, 23.5% oxygen and 11.77% sulfur.

An infrared spectrum (FIG. 1) of thienamycin, as a nujol mull, reveals the following absorption peaks:

| | |
|---|---|
| sharp peak at | 1765 cm.$^{-1}$ |
| broad peaks at | 1650 – 1550 cm.$^{-1}$; |
| | 2800 – 2500 cm.$^{-1}$ and |
| | 3500 – 3100 cm.$^{-1}$. |

Other bands are found at: 1290, 1245, 1150–1130, 1065, 995, 970, 945–935, 885, 805, 785 and 720 cm.$^{-1}$.

An NMR spectrum at 100 MHz of thienamycin lyophilized from $D_2O$ and examined at a concentration of 1.5 mg./0.4 ml. $D_2O$, containing a trace of the internal standard sodium, 2,2-dimethyl-2-silapentane-5-sulfonate, reveals the following peaks: $\delta$ 1.275, d, 3H, J=6.8; $\delta$ 3.15, m, 6H; $\delta$ 3.39, d, d, 1H, J=6.0, 2.9; $\delta$ 4.20, m, 2H.

Thienamycin has a specific optical rotation $[\alpha]_D^{27°\,C.}$ + 82.7 (C = 0.1%, w/v, in a 10 mM. aqueous phosphate buffer, pH 6.95).

Optical rotatory dispersion reveals a single, positive Cotton effect with a peak at 311 nm and a trough at 242 nm. Circular dichroism reveals a positive maximum at 287.5 nm and a negative minimum at 216 nm.

The ultraviolet absorption spectrum of thienamycin taken in aqueous solution in the pH range 4 to 8, has a peak at 296.5 nm ($E_{1cm.}^{1\%}$ = 290, $\epsilon$ = 7900) and a trough at 242 nm ($E_{1cm.}^{1\%}$ = 88). Spectra taken immediately following preparation of solutions at pH 2 show a red-shift in the absorption maximum to 309 nm. Spectra taken immediately following adjustment to pH 12 show a red-shift of the absorption maximum to 300.5 nm.

Thienamycin is an internally neutralized amphoteric substance, whose acidic function has a $pKa_1$ = 3.08 when measured in 30 mM. phosphate buffer, taking advantage of the pH induced shift in ultraviolet absorption spectrum.

Positive color reactions are obtained with ninhydrin, iodoplatinate and Folin reagents. A negative Sakaguchi test is observed.

When thienamycin is subjected to thin layer chromatography on cellulose plates containing a fluorescent indicator and developed with ethanol:water (70:30), it is detected at an $R_f$ value of 0.45 to 0.50 by each of the following criteria employed separately: (1) Bioautography on agar plates seeded with detector organism *Staphylococcus aureus* MB-108, hereinafter referred to as *Staphylococcus aureus* ATCC 6538P (2) the quenching of fluorescence excited by incident ultraviolet light, (3) a peach-colored reaction following ninhydrin spray and heating, (4) a slow bleaching of the iodoplatinate spray reagent.

The mobility of thienamycin in several additional chromatography systems are set forth below:

| Solvent System | Adsorbent | $R_f$ |
|---|---|---|
| Butanol:acetic acid:water (40:10:50) | Avicel TLC | 0.43 |
| Ethanol:water (70:30) | Silica Gel G | 0.49 |
| | Avicel TLC | 0.48 |
| n-propanol:water (70:30) | Silica Gel G | 0.31 |
| | Avicel TLC | 0.36 |
| Ethanol:water (70:30) | Whatman #1 descending paper chromatogram | 0.63 |
| Ethanol:water (70:30) | TLC Silica Gel HF (Analtech) TLC pre-washed with EtOH | 0.44 |

Avicel is an American Viscose Corporation trademark for crystalline cellulose. The $R_f$ values refer to the distance from the origin to the center of bioactivity (as determined by bioautography on *Staphylococcus aureus* ATCC 6538P divided by the distance from the origin to the solvent front.

Amino acid analysis of an acid hydrolysate of thienamycin conducted on a model KLA-5 Hitashi-Perkin-Elmer analyzer reveals one major ninhydrin-reactive component, having a retention time midway between that of alanine and glycine and producing a ninhydrin reaction product whose absorbance measured at 440 nm is threefold greater than that measured at 540 nm. When the antibiotic is treated with cold performic acid followed by hydrogen bromide prior to acid hydrolysis, in a manner typically used to convert thio-ethers and sulfhydryls to sulfones and sulfonic acids, respectively, amino acid analysis reveals one major ninhydrin-reactive component having a retention time just greater than that of aspartic acid, and with reaction product absorbancies measured at 540 nm which are 3.2 fold greater than those measured at 420 nm. This component is identical to taurine (2-aminoethanesulfonic acid) by comparison with the elution time of an authentic sample which had been submitted to the identical sequence of oxidation and acid hydrolysis. From this comparison, it is estimated that the proportion of taurine recovered was 0.8 μmole for each mg. of thienamycin entering the reaction sequence.

Thienamycin shows an optimum stability in aqueous solution when it is kept at concentrations below 1 mg./ml. and in the presence of phosphate buffers which assure a resultant pH between 6 and 7. For example, a 1 mg./ml. solution in water (pH 7.0), stored at 0° C., has a half-life of 20 days whereas at the same concentration in 10 mM. potassium phosphate, pH 7.0, the half-life is extended to 37 days. However, when a 12 mg./ml. solution of antibiotic in 10 mM. phosphate buffer is stored at 10° C., it shows a half-life of only 3 days. This solution, initially pale yellow, acquires a deep amber coloration by the 48th hour of storage.

The half-life of thienamycin in the pH range below neutrality and at room temperature is: 346 minutes, pH 4.0; 30 minutes, pH 3.0; 6.7 minutes, pH 2.0, where in each case a 30 mM. phosphate buffer is used to establish hydrogen ion control. Above neutrality and at 30° C. the half-life is: 10 minutes, pH 8.2; 5.7 minutes, pH 8.8 (borate buffer) and 2.1 minutes, pH 12 (0.01M sodium hydroxide).

Antibiotic activity and ultraviolet absorbance, measured at 296.5 nm, are extinguished in strict proportion, and with a half-life of 5.7 minutes in reaction mixtures initially containing 0.05 μmoles of antibiotic and 4 μmoles of hydroxylamine per ml. and incubated at pH 7.0 and 20° C. A half-life of 2.5 minutes is observed when the reagent is cysteine, 4 μmoles per ml., at pH 7.0 and 20° C. Finally, antibiotic activity and absorbance are extinguished on exposure to preparations of β-lactamase obtained by the sonic disintegration of a strain of *Enterobacter cloacae*.

Thienamycin is believed to have a molecular structure as follows:

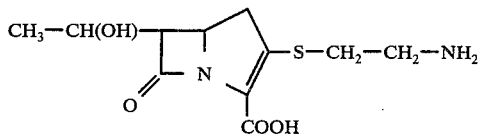

Thienamycin is further characterized by the following antibiotic spectrum profile. The test employs the Bauer-Kirby disc diffusion method modified only in respect to the 2 mm. agar depth employed here. The results, expressed in terms of the diameter in millimeters of the zone of inhibition are as set forth in Table 1.

TABLE 1

| | | Antibiotic Preparation** | | |
|---|---|---|---|---|
| | | I | II | III |
| | Antibiotic | μg. antibiotic/disc*** | | |
| Organism | resistance* | 12 | 9.7 | 6.6 |
| *Staphylococcus aureus* | 2985 | — | 39 | 39 | 38 |
| *Staphylococcus aureus* | 2314 | P | 40 | 39 | 38 |
| *Streptococcus faecalis* | 755 | — | 27.5 | 26 | 24 |
| *Bacillus subtilis* | 964 | — | 48.5 | 48 | 46 |
| *Escherichia coli* | 2017 | — | 30 | 29 | 28 |
| *Escherichia coli* | 2964 | P, C | 28 | 27 | 27 |
| *Escherichia coli* | 2482 | — | 30 | 28 | 27 |
| *Klebsiella* | 2921 | P | 26 | 25 | 25 |
| *Klebsiella* | 2922 | P | 26 | 25 | 25 |
| *Enterobacter cloacae* | 2646 | P, C | 26 | 26 | 25 |
| *Enterobacter cloacae* | 2647 | — | 30 | 30 | 27.5 |
| *Proteus mirabilis* | 2830 | P, C | 23 | 22 | 21 |
| *Proteus morganii* | 2833 | P, C | 23.5 | 22 | 20 |
| *Serratia* | 2840 | P, C | 25 | 24 | 23 |
| *Pseudomonas aeruginosa* | 2824 | P, C | 31 | 32 | 30 |
| *Pseudomonas aeruginosa* | 3210 | P, C | 27 | 27 | 25 |
| *Pseudomonas aeruginosa* | 2616 | P, C | 23 | 22 | 20.5 |

*P = Penicillins as represented by ampicillin
C = Cephalosporins as represented by cephalothin
**I: Crude preparation (310 units/mg.)
II: Intermediate purity (13,200 units/mg.).
III: Substantially pure (estimated 31,000 units/mg.). The unit of antibacterial potency is defined in the succeeding section labelled ASSAY.
***: Calculated on the basis of hydroxylamine-extinguishable absorbance described below.

A further evaluation of substantially pure antibiotic employed the agar dilution method. An inoculum of 2 × 10⁴ to 1 × 10⁵ organisms is applied as a 0.002 ml. droplet to the surface of Mueller-Hinton agar containing serial, twofold dilutions of antibiotic over the range 0.01 to 73 μg./ml. The results (Table 2) are reported as the minimum inhibitory concentration, in μg./ml., that being the lowest antibiotic concentration at which the growth of the test organism is inhibited over a period of 18 hours at 37° C.

TABLE 2

| Test Organism | | Antibiotic resistance* | Minimum Inhibitory Concentration (μg./ml) |
|---|---|---|---|
| *Staphylococcus aureus* | 2314 | P | 0.02 |
| *Escherichia coli* | 2482 | — | 0.3 |
| *Escherichia coli* | 2964 | P, C | 0.3 |
| *Escherichia coli* | 2017 | — | 0.15 |
| *Klebsiella* | 2921 | P | 0.3 |
| *Klebsiella* | 2922 | P | 0.3 |
| *Proteus mirabilis* | 2830 | P, C | 4.7 |
| *Serratia* | 2840 | P, C | 4.7 |
| *Pseudomonas aeruginosa* | 2824 | P, C | 0.6 |
| *Pseudomonas aeruginosa* | 2616 | P, C | 4.7 |
| *Pseudomonas aeruginosa* | 3210 | P, C | 2.4 |

*P = Penicillins as represented by ampicillin
C = Cephalosporins as represented by cephalothin Thienamycin exhibits in vivo activity against gram-negative and gram-positive organisms and hence is useful in controlling bacterial infections in host animals. In determining the in vivo activity, thienamycin is dissolved in and diluted with 0.15M NaCl, 0.01M sodium phosphate, pH 7.0, to provide five fourfold concentrations of drug for testing. Female white Swiss mice, averaging about 21 g. in weight, were infected intraperitoneally and subcutaneously with the test organism suspended in broth. The numbers of organisms injected were determined by standard plate-count techniques. At the time of infection, and again 6 hours later, certain of the mice were treated intraperitoneally, subcutaneously and orally with the antibiotic. Five mice were used for each concentration of drug tested. An additional two mice, not infected, were treated with the antibiotic to determine whether the amount of agent injected was toxic. Controls of five mice for each of several dilutions of the infecting culture were included in each test in order to calculate the numbers of organisms that were lethal to 50% of the infected, untreated mice ($LD_{50}$). This calculation was made using survival data of the seventh day after infection, at which time the amount of drug that should protect 50% of the infected mice ($ED_{50}$) also was calculated.

All animals receiving this challenge and not treated with antibiotic died within 48 hours of the infection. The efficacy of thienamycin having a potency of 30,000 units per mg. is recorded in Table 3:

TABLE 3

Efficacy Studies (mice)[a]

| Organism | No. $LD_{50}$ | Route of treatment, doses | $ED_{50}$ mg./kg./dose |
|---|---|---|---|
| Staph. aureus 2949 | 7 | i.p.x2 | 0.012 |
|  | 7 | s.c.x2 | 0.08 |
|  | 13 | p.o.x2[β] | 0.67 |
| Pseudomonas aeruginosa 3210 | 7 | i.p.x3[a] | 0.45 |
|  | 7 | s.c.x3 | 2.05 |
| E. coli 2017 | 9 | i.p.x2 | 0.375 |

[a] = x3, indicates treatment at the time of infecting dose, and at 2 hours and 4 hours after that event.
x2, indicates treatment at the time of infecting dose and again 6 hours later.
[β] = Animals are fasted 24 hours prior to infection and therapy.

A low order of mammalian toxicity was established by the observation of no adverse effects during a 7 day period following the intravenous administration of 500 mg. of antibiotic per kg. body weight in the mouse.

Thienamycin is a valuable antibiotic active against various gram-positive and gram-negative bacteria and, accordingly, finds utility in human and veterinary medicine. The compound of this invention can be used as antibacterial drugs for treating infections caused by gram-positive or gram-negative bacteria, for example against *Staphylococcus aureus, Proteus mirabilis, Escherichia coli, Klebsiella pneumoniae, Pseudomonas aeruginosa* and *Enterobacter cloacae*. The antibacterial material of the invention may further be utilized as additives to animal feedingstuffs, for preserving foodstuffs and as disinfectants. For example, it may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of deleterious bacteria.

The antibiotic of this invention may be used in any one of a variety of pharmaceutical preparations as the sole active ingredient or in combination either with one or more other antibiotics or with one or more pharmacologically active substances. As an example of the former, an aminocyclitol antibiotic such as gentamicin may be coadministered in order to minimize any chance that resistant organisms will emerge. As an example of the latter, diphenoxylate and atropine may be combined in dosage forms intended for the therapy of gastroenteritis. The antibiotic may be employed in capsule form or as tablets, powders or liquid solutions or as suspensions or elixirs. It may be administered orally, topically, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the composition may, for example, be formulated as an intramammary preparation in either long acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

In the treatment of bacterial infections in man, the compound of this invention is administered orally or parenterally, in accordance with conventional procedures for antibiotic administration, in an amount of from about 2 to 600 mg./kg./day and preferably about 5 to 100 mg./kg./day in preferably divided dosage, e.g. three to four times a day. They may be administered in dosage units containing, for example, 25, 250, 500 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

The antibiotic containing fermentation broths produced in accordance with the procedures described herein have activities ranging from about 50 to 400 units per ml. when assayed in accordance with the disc-diffusion assay using *Staphylococcus aureus* ATCC 6538P. Antibiotic preparations having at least 2 units per mg. activity can be purified and the antibiotic recovered by a number of procedures. One such procedure comprises adsorbing thienamycin on a strongly cationic exchange resin. Illustrative of such resins are those of the sulfonate type having a styrene-divinylbenzene matrix, for example the polystyrene nuclear sulfonic acid resin Dowex 50 × 2 (manufactured by Dow Chemical Co., Midland, Mich.), on the sodium cycle. Other representative members of the class of strongly cationic exchange resins include the following: Dowex 50 × 4, Dowex 50 × 8 (manufactured by Dow Chemical Co., Midland, Mich.), Amberlite IR120 (manufactured by Rohm & Haas Co., Philadelphia, Pa.), Duolite C25D (manufactured by Chemical Process Co., Redwood City, Calif.), Permutit Q (manufactured by Permutit Co., Birmingham, N.J.), Ionac C249 (manufactured by Ionac Chemical Co., Birmingham, N.J.) and Amberlite 200.

A method of obtaining further purified thienamycin is by the use of gel filtration through polyacrylamide gel having a pore size which excludes molecules having a molecular weight greater than 1800. A preferred gel is Bio-Gel P-2 (manufactured by Bio.Rad, Richmond, Calif.).

The adsorbed antibiotic is readily eluted from the cationic exchange resin with aqueous solutions of ammonia or of organic bases such as pyridine, picolines, lutidines, collidines and alkyl amines. The eluate so obtained can be further purified, if desired, by other purification procedures. Thus, the eluate can be purified by passing it through polyester polymers such as XAD-7 or 8 or through polystrene, hydrophobic crosslinked divinyl benzene polymers such as XAD-1, 2 and 4, preferably XAD-2.

A preferred method for recovering purified thienamycin is to pass a solution of the antibiotic, such as the filtered fermentation broth, the pH of which has been adjusted between 4 to 5 through a column containing a strong cation exchange resin of the sulfonate type in the sodium cycle (Dowex 50 × 2). The resulting adsorbate is then eluted with a suitable eluant such as 2% aqueous pyridine. The eluates are collected in fractions, the size of the fraction depending upon the size of the column employed. Further purification may be achieved by a sequence of processes involving the following chromatographic media: anion exchange resins of the polystyrene-trimethylammonium type (e.g. Dowex-1 in the chloride cycle), cation exchange resins of the polystyrene-sulfonate type (e.g. Dowex-50 in the 2,6-lutidinium cycle), gel-permeation resins (e.g. BioGel P-2, a polyacrylamide resin) and polymeric absorbents (e.g. XAD-2, a polystyrene resin). The bioactivity of the eluates is measured by assaying the eluate using *Staphylococcus aureus* ATCC 6538P as the assay organism.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of an identical product should be construed as constituting an analogous method. The described processes are capable of wide variation and modification and any minor departure or extension is considered as being within the skill of the artisan and as falling within the scope of this invention.

ASSAY

Assays of antibacterial activity are run according to the following disc-diffusion procedure unless otherwise indicated. The assay plates are prepared in the following manner. An overnight growth of the assay organism, *Staphylococcus aureus* ATCC 6538P, in nutrient broth plus 0.2% yeast extract is diluted with nutrient broth plus 0.2% yeast extract to a suspension having 55% transmittance at a wavelength of 660 m$\mu$. This suspension is added to Difco nutrient agar supplemented with 2.0 g./l. Difco yeast extract, at 47° C. to 48° C., to make a composition containing 33.2 ml. of the suspension per liter of agar. Five ml. of this suspension is poured into petri dishes of 85 mm. diameter, and these plates are chilled and held at 4° C. until used (5 day maximum).

Samples of the antibiotic to be assayed are diluted to an appropriate concentration in phosphate buffer at pH 7. Filter-paper discs, 0.5-inch in diameter, are dipped into the test solution and placed on the surface of the assay plate; two discs for each sample are normally placed on one plate opposite to one another. The plates are incubated overnight at 37° C. and the zone of inhibition is measured as mm. diameter. The zone of inhibition measured in mm. determines relative potencies or, when compared with a purified reference standard such as cephalothin, the potency of antibiotic in units/ml. The unit of activity reported in Examples 4 through 7 is based on cephalothin standard solutions of 8, 4, 2 and 1 $\mu$g./ml. One unit is defined as the amount which calculates to produce the same inhibition as 1 $\mu$g. of cephalothin/ml. that zone of inhibition being between 16 and 21 mm. diameter.

EXAMPLE 1

A tube of lyophilized culture of *Streptomyces cattleya* is opened aseptically and the contents suspended in a tube containing 0.7 ml. of sterile Davis salts having the following composition:

| Davis Salts | | |
|---|---|---|
| Sodium citrate | 0.5 | g |
| K$_2$HPO$_4$ | 7.0 | g |
| KH$_2$PO$_4$ | 3.0 | g |
| (NH$_4$)$_2$SO$_4$ | 1.0 | g |
| MgSO$_4$ . 7H$_2$O | 0.1 | g |
| Distilled H$_2$O | 1000 | ml |

A 0.2 ml. portion of this suspension is used to inoculate a culture slant of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| MgSO$_4$ . 7H$_2$O | 0.05 | g |
| Distilled H$_2$O | 1000 | ml |

-continued

| Medium A | |
|---|---|
| pH: adjust to 6.5 using NaOH | |

*Ardamine: Yest Products Corporation

| +Phosphate Buffer Solution | |
|---|---|
| $KH_2PO_4$ | 91.0 g |
| $Na_2HPO_4$ | 95.0 g |
| Distilled $H_2O$ | 1000 ml |
| For Slants: add agar - 25.0 g/l | |

The inoculated slant is incubated for 8 days at 28° C. and then stored at 4° C.

A portion of the spores and aerial mycelia of this slant is used to inoculate a baffled 250 ml. Erlenmeyer seed flask containing 50 ml. of Medium A (without agar). This seed flask is shaken at 28° C. on a 220 rpm shaker (2 inch throw) for two days at which time the growth is satisfactory.

Fifteen 250 ml. Erlenmeyer flasks, each containing 40 ml. of Medium B, are inoculated with 1 ml. per flask of the growth from the seed flask. The Medium B has the following composition:

| Medium B | |
|---|---|
| Corn Meal | 20.0 g |
| Distiller's Solubles | 10.0 g |
| Soybean Meal | 15.0 g |
| Sodium Citrate | 4.0 g |
| $CaCl_2 . 2H_2O$ | 0.5 g |
| $MgSO_4 . 7H_2O$ | 0.1 g |
| $CoCl_2 16H_2O$ | 0.01 g |
| $FeSO_4 . 7H_2O$ | 0.01 g |
| **Polyglycol 2000 | 0.25% by Vol. |
| Distilled $H_2O$ | 1000 ml |
| pH: adjust to 6.5 using NaOH | |

**Polyglycol 2000: Dow Chemical Co.

These 15 production flasks are shaken at 28° C. on a 220 rpm shaker (2 inch throw) for up to 3 days with assays performed during the fermentation cycle. Assays are performed using centrifuged broth. Prior to assay, the pH of the broth is adjusted as shown in the following table.

| Age (Hours) | 48 | 53 | 72 |
|---|---|---|---|
| Activity vs ATCC 6538P (mm. zone) | 34/40h | 35/41h | 34 |
| pH, initial | 6.3 | 5.9 | 5.0 |
| pH, adjusted | — | 6.8 | 6.2 | h = hazy

At 53 hours age, the broths from 13 flasks are pooled. An aliquot is centrifuged and assayed. The remaining broth is filtered, adjusted to pH 7, and 500 ml. is freeze-dried to yield 10.7 g. of solids. A 1.5 g. portion of these solids is taken up in 25 ml. of n-butyl alcohol:water (1:99). The pH of the solution is 7.0. This solution is applied to a 5 × 118 cm. column of BioGel P-2 (200–400 mesh) which has previously been equilibrated with n-butyl alcohol:water. The gel is developed with the same solution at 10 ml./min. collecting a 650 ml. forerun followed by 75 fractions of 20 ml. each. The effluent stream is monitored with a Mecco-matic recording differential refractometer. Each fraction is assayed for antibacterial activity. Thienamycin is found in fractions 34 through 40 with a maximum in fraction 37. Ten ml. of fraction 37 are freeze-dried to yield 2.0 mg. of solids. The solids obtained are taken up in 5 ml. of water for assay. Assay plates are incubated overnight at 28° C. The results are tabulated below:

| Concentration | Zone size in mm. vs. *Staph. Aureus* ATCC 6538P |
|---|---|
| 80 μg./ml. | 30 mm |
| 40 μg./ml. | 25 mm |
| 20 μg./ml. | 21 mm |
| 10 μg./ml. | 17 mm |

EXAMPLE 2

A tube of lyophilized culture of *Streptomyces cattleya* is opened aseptically and the contents suspended in 0.8 ml. of sterile Davis salts having the following composition:

| Davis Salts | |
|---|---|
| Sodium citrate | 0.5 g |
| $K_2HPO_4$ | 7.0 g |
| $KH_2PO_4$ | 3.0 g |
| $(NH_4)_2SO_4$ | 1.0 g |
| $MgSO_4 . 7H_2O$ | 0.1 g |
| Distilled $H_2O$ | 1000 ml |

This suspension is used to inoculate 4 slants of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| $MgSO_4 . 7H_2O$ | 0.05 | g |
| Distilled $H_2O$ | 1000 | ml |
| pH: adjust to 6.5 using NaOH | | |

*Ardamine: Yest Products Corporation

| +Phosphate Buffer Solution | |
|---|---|
| $KH_2PO_4$ | 91.0 g |
| $Na_2HPO_4$ | 95.0 g |
| Distilled $H_2O$ | 1000 ml |
| For Slants: add agar - 25.0 g/l | |

The inoculated slants are incubated for one week at 28° C. and then stored at 4° C.

A portion of the spores and aerial mycelia of one of the slants is used to inoculate a baffled 250 ml. Erlenmeyer seed flask containing 50 ml. of Medium A. This seed flask is shaken at 28° C. on a 220 rpm shaker (2 inch throw) for two days at which time the growth is satisfactory.

Fifteen 250 ml. Erlenmeyer flasks each containing 40 ml. of Medium B, are inoculated with 1 ml. per flask of the growth from the seed flask. The Medium B has the following composition:

| Medium B | |
|---|---|
| Corn Meal | 20.0 g |
| Distiller's Solubles | 10.0 g |
| Soybean Meal | 15.0 g |
| Sodium Citrate | 4.0 g |
| $CaCl_2 . 2H_2O$ | 0.5 g |
| $MgSO_4 . 7H_2O$ | 0.1 g |
| $CoCl_2 . 6H_2O$ | 0.01 g |
| $FeSO_4 . 7H_2O$ | 0.01 g |
| **Polyglycol 2000 | 0.25% by Vol. |
| Distilled $H_2O$ | 1000 ml |
| pH: adjust to 6.5 using NaOH | |

**Polyglycol 2000: Dow Chemical Co.

These flasks are shaken at 28° C. on a 220 rpm shaker (2 inch throw) for up to three days with assays performed during the fermentation cycle. Assays are performed using the supernatant of centrifuged broth. The results are as follows:

| Age (Hours) | 48 | 53 | 72 |
|---|---|---|---|
| pH | 6.7 | 6.4 | 5.5 |
| Activity vs ATCC 6538P | 38 | 40 | 38 mm. |

At 53 hours age, the broths from 13 flasks are pooled and filtered. The pH of a 400 ml. portion of the filtrate is adjusted to 4.8 with dilute HCl, and this is adsorbed on 140 ml. of Dowex 50 × 2 Na$^+$ at the rate of 14 ml./min. The adsorbate is washed with 200 ml. of deionized water and eluted with 2% pyridine in water collecting 6 × 70 ml. fractions. The pH of the fractions is adjusted to 7.0.

Assays are run on all fractions and the zone diameters are tabulated below:

| Filtered Broth | |
|---|---|
| Dilution | Zone Diameter |
| 1:4 | 33 mm |
| 1:8 | 30 mm |
| 1:16 | 27 mm |
| 1:32 | 24 mm |

| Eluate Fractions | | |
|---|---|---|
| Dilution | | Zone Diameter |
| 1. | 1:5 | 22.5 mm |
| 2. | 1:5 | 36 mm |
| 3. | 1:5 | 20 mm |
| 4,5 & 6 | 1:5 | 0 mm |

These assays indicate that 45% of the activity is in the eluates. Eluate fraction #2 is freeze-dried to yield 117 mg. of solids.

The 117 mg. of solids are dissolved in 1.5 ml. of n-butyl alcohol:water (1:99). The solution is applied to a bed of Bio-Gel P-2 1.4 × 81.5 cm. which has been previously equilibrated with n-butyl alcohol:water. The gel is developed with n-butyl alcohol:water at 1 ml./min. collecting 2 ml. fractions. The effluent stream is monitored with a Mecco-matic recording refractometer. Fractions are assayed for antibacterial activity at a dilution of 1:20. The bioactive peak is observed spanning fractions 44 through 53. Fractions 46 through 49 and half of fraction 50 are combined. A one ml. sample of the combined fractions is removed for reassay and the remainder freeze-dried to yield 4.2 mg. of partially purified antibiotic.

EXAMPLE 3

A tube of lyophilized culture *Streptomyces cattleya* is opened aseptically and the contents suspended in 0.8 ml. of sterile Davis salts having the following composition:

| Davis Salts | |
|---|---|
| Sodium citrate | 0.5 g |
| K$_2$HPO$_4$ | 7.0 g |
| KH$_2$PO$_4$ | 3.0 g |
| (NH$_4$)$_2$SO$_4$ | 1.0 g |
| MgSO$_4$ . 7H$_2$O | 0.1 g |
| Distilled H$_2$O | 1000 ml |

This suspension is used to inoculate four slants of Medium A (plus agar) having the following composition:

| Medium A | | |
|---|---|---|
| Yeast Autolysate (Ardamine*) | 10.0 | g |
| Glucose | 10.0 | g |
| $^+$Phosphate Buffer | 2.0 | ml |
| MgSO$_4$ . 7H$_2$O | 0.05 | g |
| Distilled H$_2$O | 1000 | ml |
| pH: adjust to 6.5 using NaOH | | |

*Ardamine: Yeast Products Corporation

| $^+$Phosphate Buffer Solution | |
|---|---|
| KH$_2$PO$_4$ | 91.0 g |
| Na$_2$HPO$_4$ | 95.0 g |
| Distilled H$_2$O | 1000 ml |
| For Slants: add agar - 25.0 g/l | |

The inoculated slants are incubated for one week at 28° C. and stored at 4° C. A portion of the spores and aerial mycelia of one of the slants is used to inoculate three baffled 250 Erlenmeyer seed flasks, each containing 50 ml. of Medium A. These seed flasks are shaken at 28° C. on a 220 rpm shaker (2 inch throw) for one day at which time the growth is satisfactory.

Twelve 2000 ml. Erlenmeyer flasks, each containing 250 ml. of Medium C, are each inoculated with 7 ml. of suspension obtained by the aseptic pooling of the contents of the 3 seed flasks. The Medium C has the following composition:

| Medium C | | |
|---|---|---|
| Corn Meal | 20.0 | g |
| Distiller's Solubles | 10.0 | g |
| Soybean Meal | 15.0 | g |
| CaCl$_2$ . 2H$_2$O | 0.5 | g |
| MgSO$_4$ . 7H$_2$O | 0.1 | g |
| CoCl$_2$ . 6H$_2$O | 0.01 | g |
| FeSO$_4$ . 7H$_2$O | 0.01 | g |
| CaCO$_3$ | 4.0 | g |
| Polyglycol 2000 | 0.25% | by Vol. |
| Distilled H$_2$O | 10000 | ml |
| pH: adjust to 6.5 using NaOH | | |

These flasks are shaken at 28° C. on a 220 rpm shaker (2 inch throw) for 72 hours. The broths are pooled, and an aliquot centrifuged for assay. The harvested broth has a pH of 7.4 and the antibacterial assay using the supernatant of centrifuged broth is 43 mm.

The broth is filtered and the pH of the filtrate adjusted to 4.0 with dilute HCl and 3000 ml. is adsorbed on 300 ml. of Dowex 50 × 2 Na$^+$ at the rate of 30 ml./min. the adsorbate is washed with 300 ml. of deionized water and eluted with 2% pyridine collecting 8 × 150 ml. fractions. The pH of the fractions is adjusted to 7.0. Eluate fractions #2 and #3, comprising 300 ml. are pooled and contain 48% of the total bioactive material applied on the Dowex 50 × 2 Na$^+$ column.

A 280 ml. portion of the pooled fractions of Dowex 50 × 2 Na$^+$ eluate at pH 7.0, obtained above is percolated through a 40 ml. column of Dowex 1 × 2 Cl$^-$ cycle resin. The resin is washed with 160 ml. of deionized water. The effluent and wash fractions are combined to give 440 ml. of solution. This solution is adjusted to pH 8.2 with dilute sodium hydroxide, concentrated under reduced pressure to 300 ml., adjusted to pH 7.0 with dilute HCl and freeze-dried to yield 189 mg. of solids.

The freeze-dried solids, 189 mg., obtained above are dissolved in n-butyl alcohol:water (1:99). The solution, 25 ml., is applied to a column of Bio-Gel P-2 (200–400 mesh), 5 × 108 cm. which has previously been equilibrated with n-butyl alcohol:water. The gel is then developed with n-butyl alcohol:water at 6.7 ml./min. The effluent stream is monitored with a Mecco-matic recording differential refractometer. A five-hundred ml. forerun is taken followed by fractions of 20 ml. each. Every fraction is assayed for antibacterial activity at a dilution of 1:25. The bio-activity is observed in fractions 37 through 42, having a maximum at fraction 39. Fractions 38 through 41, having a total volume of 80 ml., are combined. This solution is concentrated to 10 ml. at pH 7.0 and freeze-dried. The freeze-dried solid, 13.5 mg., has a relative potency approximately sixfold higher than the potency of the sample charged to the Bio-Gel P-2 column based on comparison by *Staphylococcus aureus* disc-diffusion assays.

EXAMPLE 4

A tube of lyophilized culture of *Streptomyces cattleya* is opened aseptically and the contents suspended in 0.8 ml. of sterile Davis salts having the following composition:

| Davis Salts | | |
|---|---|---|
| Sodium citrate | 0.5 | g |
| K$_2$HPO$_4$ | 7.0 | g |
| KH$_2$PO$_4$ | 3.0 | g |
| (NH$_4$)$_2$SO$_4$ | 1.0 | g |
| MgSO$_4$ . 7H$_2$O | 0.1 | g |
| Distilled H$_2$O | 1000 | ml. |

This suspension is used to inoculate four slants of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| MgSO$_4$ . 7H$_2$O | 0.05 | g |
| Distilled H$_2$O | 1000 | ml |
| pH: adjust to 6.5 using NaOH | | |

*Ardamine: Yeast Products Corporation

| +Phosphate Buffer Solution | | |
|---|---|---|
| KH$_2$PO$_4$ | 91.0 | g |
| Na$_2$HPO$_4$ | 95.0 | g |
| Distilled H$_2$O | 1000 | ml |
| For Slants: add agar - 25.0 g/l | | |

The inoculated slants are incubated for one week at 28° C. and then stored at 4° C.

Ten ml. of Medium A is transferred aseptically to one of these slants, the spores and aerial mycelia scraped into suspension, and 3.3 ml. of this suspension used to inoculate a 2 liter baffled Erlenmeyer flask containing 500 ml. of Medium A. This seed flask is shaken at 28° C. on a 160 rpm shaker (2 inch throw) for 48 hours at which time the growth is satisfactory.

The growth from this seed flask is used to inoculate a 190 liter stainless steel seed tank containing 160 liters of Medium A. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1%. pH determinations are made as follows:

| Age, Hours | 0 | 12 | 24 |
|---|---|---|---|
| pH | 6.4 | 6.4 | 6.3 |

Forty-three liters of the growth in this seed tank is used to inoculate a 756 liter stainless steel fermentor containing 467 liters of Medium E, wherein Medium E has the composition:

| Medium E | | |
|---|---|---|
| Cerelose | 25.0 | g |
| Corn Steep Liquor (wet basis) | 15.0 | g |
| Distiller's Solubles | 10.0 | g |
| Cottonseed Media (Pharmamedia) | 5.0 | g |
| CoCl$_2$ . 6H$_2$O | 0.01 | g |
| CaCO$_3$ (after pH adjustment) | 3.0 | g |
| Polyglycol 2000 | 0.25% | |
| Tap wate | 1000 | ml |
| pH: adjust to 7.3 using NaOH | | |

This tank is run at 24° C. using an agitation rate of 95 rpm and an airflow of 10 cu. ft. per minute for 120 hours. Additional defoamer, Polyglycol 2000, is added as required, not to exceed 0.1%. Antibacterial assays are run and the data is as follows:

| Age | pH | Antibiotic Activity vs ATCC 6538P (mm) | Dextrose mg./ml. |
|---|---|---|---|
| 0 | 6.8 | — | 22 |
| 12 | 6.6 | — | 21.3 |
| 24 | 6.2 | — | 16.5 |
| 36 | 5.8 | 25 | 12.1 |
| 48 | 5.7 | 25 | 7.8 |
| 60 | 5.8 | 21.5 | 4.3 |
| 72 | 6.1 | 25 | 2.5 |
| 84 | 6.6 | 33 | 1.6 |
| 96 | 6.7 | 41.5 | 1.0 |
| 108 | 6.5 | 45 | 1.0 |
| 120 | 6.5 | 45 | 0.5 |

Four-hundred liters of whole broth is filtered using a filter press and filter aid admix. 1.2 G. of (ethylenedinitrilo) tetraacetic acid, sodium salt is added to the filtrate. The filtrate is cooled to 6° C., adjusted to pH 4.0 ± 0.2 and maintained at 6° C. The cold filtrate is adsorbed on 38 liters of Dowex 50 × 4 Na$^+$, 20–50 mesh at 4 liters/minute. The adsorbate is washed with 40 liters of deionized water. The adsorbate is eluted with 2% aqueous pyridine and three fractions of 19 liters each are collected and assayed. The antibacterial assay indicates that eluate fractions 2 and 3 contain 22% of the applied activity. These fractions are combined, concentrated to 3.8 liters and adjusted to pH 7.

The 3.8 liter concentrate obtained above is adsorbed on 2.5 liters of Dowex 1 × 2, 50 to 100 mesh, chloride cycle resin at 200 ml./min. The resin is eluted with deionized water at the same rate. Ten one liter fractions are collected and each fraction adjusted to pH 7.0 as required. Assays indicate 75% of the bio-activity is in fractions 5 through 8. These fractions are combined and filtered using a 0.45 micron Millipore. A 3 liter portion of this filtrate is freeze-dried to yield 16.6 grams of solids having a potency of 70 units/mg.

Four grams of freeze-dried solids obtained above are taken up in 50 ml. of 0.1M 2,6-lutidine acetate buffer.

The solution at pH 6.3, is applied to a Dowex 50 × 8 column prepared as follows:

A 2.5 liter amount of Dowex 50 × 8 (200–400 mesh) hydrogen cycle resin is converted to the 2,6-lutidine cycle. The resin is equilibrated with five column volumes of 0.1M 2,6-lutidine acetate, pH 6.3, buffer. The dimensions of the equilibrated resin bed are 5 × 114 cm. The column is developed with 0.1M buffer at 14 ml./min.

The effluent stream is monitored with a Mecco-matic recording differential refractometer. The development is carried out until 220 fractions, 20 ml. each, are collected. Every other fraction from 44 through 142 is assayed at a dilution of 1:50. The bio-activity is observed in fractions 78 through 136, reaching a maximum in fractions 92 through 94. Fractions 82 through 116 are selected and combined to yield 700 ml. of solution. This solution is divided into two 350 ml. portions and freeze-dried.

One portion of the freeze-dried solids is dissolved in 0.1M 2,6-lutidine acetate, pH 7.0 buffer. The solution, 27 ml., is applied to a column of Bio-Gel P-2 (200–400 mesh) 5 × 108 cm. which has previously been equilibrated with 0.1M buffer. The gel is then developed with the same buffer at 10 ml./min.

The effluent stream is monitored with a Mecco-matic recording differential refractometer. The development is continued until 105 fractions, 20 ml. each, are collected. Every fraction from 51 through 90 is assayed at a 1:50 dilution. The assay reveals a bio-active peak in fractions 67 through 75, with a maximum in fractions 70 and 71. Fractions 68 through 75 are combined to yield a volume of 162 ml. To 145 ml. of the combined fraction, 3 ml. of 360 mM., pH 7.0 sodium phosphate buffer is added and the solution is concentrated to 9 ml. The concentrate, which contains 78% of the total bio-active material applied on the Bio-Gel P-2 column, is freeze-dried to yield 185 mg. A remaining 17 ml. aliquot of fractions 68 through 75 is freeze-dried to yield 1.9 mg. of solids which has a potency of 1050 units/mg.

EXAMPLE 5

A tube of lyophilized culture of *Streptomyces cattleya* is opened aseptically and the contents suspended to 0.8 ml. of sterile Davis salts having the following composition:

| Davis Salts | | |
|---|---|---|
| Sodium citrate | 0.5 | g |
| $K_2HPO_4$ | 7.0 | g |
| $KH_2PO_4$ | 3.0 | g |
| $(NH_4)_2SO_4$ | 1.0 | g |
| $MgSO_4 \cdot 7H_2O$ | 0.1 | g |
| Distilled $H_2O$ | 1000 | ml. |

This suspension is used to inoculate four slants of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| $MgSO_4 \cdot 7H_2O$ | 0.05 | g |
| Distilled $H_2O$ | 1000 | ml |
| pH: adjust to 6.5 using NaOH | | |

*Ardamine: Yeast Products Corporation

| +Phosphate Buffer Solution | | |
|---|---|---|
| $KH_2PO_4$ | 91.0 | g |
| $Na_2HPO_4$ | 95.0 | g |
| Distilled $H_2O$ | 1000 | ml |
| For Slants: add agar - 25.0 g/l | | |

The inoculated slants are incubated for one week at 28° C. and then stored at 4° C.

Ten ml. of Medium A is transferred aseptically to one of these slants, the spores and aerial mycelia are scraped into suspension, and 3.3 ml. of this suspension is used to inoculate a 2 liter baffled Erlenmeyer flask containing 500 ml. of Medium A. This seed flask is shaken at 28° C. on a 160 rpm shaker (2 inch throw) for 48 hours.

The growth from this seed flask is used to inoculate a 190 liter stainless steel seed tank containing 160 liters of Medium A. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1%. pH determinations are made as follows:

| Age, Hours | 0 | 12 | 24 |
|---|---|---|---|
| pH | 6.3 | 6.6 | 5.6 |

Thirty-five liters of the growth in this seed tank is used to inoculate a 756 liter stainless steel fermentor containing 467 liters of Medium E, wherein Medium E has the composition:

| Medium E | | |
|---|---|---|
| Cerelose | 25.0 | g |
| Corn Steep Liquor (wet basis) | 15.0 | g |
| Distiller's Solubles | 10.0 | g |
| Cottonseed Media (Pharmamedia) | 5.0 | g |
| $CoCl_2 \cdot 6H_2O$ | 0.01 | g |
| $CaCO_3$ (after pH adjustment) | 3.0 | g |
| Polyglycol 2000 | 0.25% | |
| Tap wate | 1000 | ml |
| pH: adjust to 7.3 using NaOH | | |

This tank is operated at 24° C. using an agitation rate of 95 rpm and an airflow of 10 cu. ft. per minute for 120 hours. Defoamer, Polyglycol 2000, is added as required, but not to exceed 0.1%. Antibacterial assays are performed and the data is as follows:

| Age | pH | Antibiotic Activity vs ATCC 6538P |
|---|---|---|
| 0 | 6.9 | — |
| 12 | 6.8 | — |
| 24 | 6.3 | — |
| 36 | 6.4 | 26 |
| 48 | 6.3 | 32 |
| 60 | 6.4 | 25 |
| 72 | 6.8 | 25 |
| 84 | 7.0 | 25 |
| 96 | 7.1 | 37 |
| 108 | 7.2 | 41.5 |
| 120 | 7.1 | 44.5 |

Four-hundred liters of the whole broth is filtered using a filter press and filter aid admix to the extent of 4% w/v. 1.2 G. of (ethylenedinitrilo) tetraacetic acid, sodium salt is added to the filtrate. The filtrate is cooled to 6° C., adjusted to pH 4.0 ± 0.2 and maintained at 6° C. The cold filtrate is adsorbed on 38 liters of Dowex 50 × 4 $Na^+$, 20–50 mesh at 4 liters/minute. The adsorbate is eluted with 2% aqueous pyridine and three fractions of 19 liters each are collected and assayed. The assays indicate 27% of input bioactivity is in fractions 2 and 3. Eluate fractions 2 and 3 are combined, concentrated to 3.7 liters and adjusted to pH 7.

The eluate concentrate of 3.7 liters is adjusted to pH 7.4 and adsorbed on 2.5 liters of Dowex 1 × 2 Cl⁻ cycle resin (50–100 mesh) at 200 ml./min. The resin is then eluted with deionized water at the same rate. Two × 2 liters; 1 × 800 ml; 1 × 4 liters and 1 × 2 liter fractions are collected, adjusting pH to 7.0 as required. Fraction 4 (4 liters), which contains 50% of the activity present in the concentrate, is filtered using a Millipore 0.45 micron filter. The clear filtrate is tray freeze-dried to yield 12.4 grams of solids which had a potency of 270 units/mg.

Four grams of the freeze-dried solids is taken up in 0.1M 2,6-lutidine acetate buffer, pH 6.3. The solution, 50 ml., restored to pH 6.3 by addition of acetic acid, is applied to a column of Dowex 50 × 8; 2,6-lutidine cycle resin (200–400 mesh) having the dimensions 5 × 114 cm. which had previously been equilibrated with 0.1M buffer. The resin is then developed with the same 0.1M pH 6.3 buffer at 14 ml./min.

The effluent stream is monitored with a Mecco-matic recording differential refractometer. Development is carried out until 150 fractions, 20 ml. each, are collected. Every other fraction from 72 through 150 is assayed at a dilution of 1:50. A single bio-active peak in fractions 76 through 148 with a maximum in fractions 92 through 102 is observed. Fractions 86 through 113 are combined to give 580 ml. of solution which contains 71% of the bio-activity applied to the Dowex 50 × 8 column. This solution is then freeze-dried.

The freeze-dried solids obtained are dissolved in 0.1M 2,6-lutidine acetate pH 7.0 buffer to make 25 ml. This solution is applied to a bed of Bio-Gel P-2 (200-400 mesh) 5 × 108 cm., which had been previously equilibrated with 0.1M buffer. The gel is then developed with the same buffer at 9 ml./min. The effluent stream is monitored with a Mecco-matic recording differential refractometer. Development is continued until 105 fractions, 20 ml. each, are collected. Every fraction, 65 through 80, is assayed at a dilution of 1:200. The bio-active peak is observed in fractions 67 through 76. Fractions 70 through 72 are combined and freeze-dried to yield 16.0 mg. with a potency of 13,800 units/mg. Fractions 69, 73 and 74 are combined and freeze-dried to yield 20.2 mg. with a potency of 5,200 units/mg.

The 16 mg. of freeze-dried solids is dissolved in 0.1M 2,6-lutidine acetate pH 7.0 buffer to make 10 ml. The solution is applied to a bed of Bio-Gel P-2, (200-400 mesh) 5 × 108 cm., which has been equilibrated with the same buffer. The gel is developed with buffer at 9 ml./min. The effluent stream is monitored with a Mecco-matic recording differential refractometer. Development is continued until 105 fractions of 20 ml. each has been collected. Every fraction, 65 through 80, is assayed at a dilution of 1:200.

The bio-active peak is observed in fractions 67 through 75. Fractions 68 through 72 are combined and freeze-dried to yield 9.1 mg. having a potency of 15,000 units/mg.

EXAMPLE 6

A tube of lyophilized culture of *Streptomyces cattleya* is opened aseptically and the contents suspended in 50 ml. of sterile Medium A contained in a 250 ml. baffled Erlenmeyer flask. Medium A has the following composition:

| Medium A | | |
|---|---|---|
| Yeast Autolysate (Ardamine*) | 10.0 | g |
| Glucose | 10.0 | g |
| Phosphate Buffer** | 2.0 | ml |
| MgSO₄ · 7H₂O | 0.05 | g |
| Distilled H₂O | 1000 | ml |
| pH: adjust to 6.5 using NaOH | | |

*Ardamine: Yeast Products Corporation

| **Phosphate Buffer Solution | | |
|---|---|---|
| KH₂PO₄ | 91.0 | g |
| Na₂HPO₄ | 95.0 | g |
| Distilled H₂O | 1000 | ml |

The inoculated flask is shaken at 28° C. on a 220 rpm (2 inches throw) for 48 hours. Forty ml. of the 48-hour broth is removed aseptically and mixed with 40 ml. of sterile 20% (v/v) glycerol. Two ml. quantities of the resulting mixture are pipetted into sterile 1 dram vials which are then frozen and stored in the vapor phase of a liquid nitrogen freezer.

Frozen vial contents are used to inoculate a 250 ml. baffled Erlenmeyer flask containing 50 ml. of Medium A. This seed flask is shaken at 28° C. on a 160 rpm shaker at 28° C. for 24 hours.

Ten ml. portions from this seed flask are used to inoculate 2 liter baffled Erlenmeyer flasks containing 500 ml. of Medium A. These seed flasks are shaken on a 160 rpm shaker at 28° C. for 24 hours.

A 1000 ml. portion of the pooled contents of these seed flasks is used to inoculate a 756 liter stainless steel fermentor containing 467 liters of Medium A. This tank is operated at 28° C. using an agitation rate of 130 rpm and an airflow of 10 cu. ft. per minute for 24 hours. Polyglycol 2000 (Dow Chemical Corp.) is used as required as a defoamer but not to exceed 0.1%. Measurements of pH and dextrose are made and are as follows:

| Age (Hours) | 0 | 12 | 24 |
|---|---|---|---|
| pH | 6.4 | 6.4 | 6.6 |
| Dextrose mg./ml. | 8.1 | 8.1 | 8.1 |

Four hundred fifty-three liters of this growth are used to inoculate a 5670 liter stainless steel fermentor containing 4082 liters of Medium E, wherein Medium E has the composition:

| Medium E | | |
|---|---|---|
| Cerelose | 25.0 | g |
| Corn Steep Liquor (wet basis) | 15.0 | g |
| Distiller's Solubles | 10.0 | g |
| Cottonseed Media (Pharmamedia) | 5.0 | g |
| CoCl₂ · 6H₂O | 0.01 | g |
| CaCO₃ (after pH adjustment) | 3.0 | g |
| Polyglycol 2000 | 0.25% | |
| Tap wate | 1000 | ml |
| pH: adjust to 7.3 using NaOH | | |

This tank is operated at 24° C. using an agitation rate of 70 rpm and an airflow of 54.3 cu. ft. per minute for 144 hours. Defoamer, polyglycol 2000, is added as required but does not exceed 0.1%. Assays are performed using the supernatent of centrifuged broth. The results are tabulated in the table below under the heading "Antibiotic Activity vs ATCC 6538P". Assays are also run by the disc-diffusion procedure using ⅜ inch filter-paper discs and 10 ml. assay plates and the results tabulated in the table below under the heading "Antibiotic Activity (10 ml. plates)". The 10 ml. assay plates are prepared as follows: An overnight growth of the assay organism, *Staphylococcus aureus* ATCC 6538P, in nutrient broth plus 0.2% yeast extract is diluted with nutrient broth plus 0.2% yeast extract to a suspension having 40% transmittance at a wavelength of 660 m$\mu$. This suspension is added to Difco nutrient agar supplemented with 2.0 g./l. Difco yeast extract, at 47° C. to 48° C., to make a composition containing 33.2 ml. of the suspension per liter of agar. Ten ml. of this suspension are poured into petri plates of 85 mm. diameter, and the plates are chilled and held at 4° C. until used (5 day maximum).

| Age | pH | Dextrose mg./ml. | Antibiotic Activity vs ATCC 6538P (mm.) | Antibiotic Activity (10 ml. plates) (mm.) |
|---|---|---|---|---|
| 0 | 6.6 | 22.2 | | |
| 12 | 6.3 | 20.2 | | |
| 24 | 5.8 | 18.0 | | 0 |
| 36 | 6.0 | 13.2 | | 21.5 |
| 48 | 6.0 | 8.6 | | 21.5 |
| 60 | 5.7 | 6.4 | | 26.5 |
| 72 | 5.8 | 2.7 | | 25.5 |
| 84 | 6.2 | 0.3 | | 27.5 |
| 96 | 6.4 | 0.2 | | 36.0 |
| 108 | 6.4 | 0 | | 35.0 |
| 120 | 6.3 | | 41.5 | 37.0 |
| 132 | 5.8 | | | 37.5 |
| 144 | 5.9 | | 43.0 | 37.5 |

The 4,082 liters of fermentation broth is filtered using a 30 inch filter press and a filter aid admix to the extent of 4% w/v. A 12 g. amount of (ethylenedinitrilo) tetraacetic acid, sodium salt is added to the filtrate. The filtrate is cooled to 6° C., adjusted to pH 4.5 ± 0.2 and maintained at 6° C. The cold filtrate is adsorbed on 480 l. of Dowex 50 × 4 Na$^+$, 20-50 mesh at about 48 l./min. The adsorbate is washed with 480 l. of deionized water and then eluted with 2% aqueous pyridine at 24 l./min. and three fractions of 300 l., 520 l. and 240 l. are collected and assayed at pH 7.0. The assays indicate that the eluate fractions contain 4%, 16% and 6%, respectively of the bioactivity applied on the Dowex 50 × 4 Na$^+$ column. Eluate fraction two is concentrated to 48 l. and adjusted to pH 7.

The 48 l. concentrate is adjusted to pH 7.3 and adsorbed on 76 l. of Dowex 1 × 2, 50 to 100 mesh, chloride cycle resin at 7.6 l./min. The resin is eluted with deionized water at the same rate. Four fractions are collected, two of 48 l., one of 70 l. and one of 48 l. The fractions are adjusted to pH 7 as collected. Assays indicate that 68% of the starting bioactivity is in the 70 l. fraction. This fraction is concentrated to 18 l. at pH 7.0 and filtered using a 0.45 micron Millipore Filter. The filtrate is tray freeze-dried to yield 99 grams of product having a potency of 310 units/mg.

Ten g. of the freeze-dried solids are taken up in 0.1M 2,6-lutidine acetate buffer, pH 6.3. The solution, 125 ml. readjusted to pH 6.3 with acetic acid, is applied to a column of Dowex 50 × 8 (200-400 mesh) in the 2,6-lutidine cycle, 7.6 × 142 cm., which had previously been equilibrated with buffer, and developed with 0.1M buffer at 25 ml./min. A 3 l. fore-cut is collected followed by 200 fractions of 20 ml. each. Every fourth fraction 36 through 192 is assayed at a dilution of 1:200. The bioactivity is contained in fractions 56 through 192, reaching a maximum in fractions 92 through 96. Fractions 80 through 136 are combined and 590 ml. of deionized water added to give 1760 ml. The pooled, diluted, solution containing 62% of the starting bio-activity applied on the Dowex 50 × 8 column, is freeze-dried.

The freeze-dried solids are dissolved in 0.1M 2,6-lutidine acetate, pH 7.0 buffer. The solution, 27 ml., is applied to a column of Bio-Gel P-2 (200-400 mesh) 5 × 112 cm. which had previously been equilibrated with 0.1M buffer. The gel is then developed with the same buffer at 10 ml./min.

The effluent stream is monitored with a Meccomatic recording differential refractometer. The development is continued until 105 fractions, 20 ml. each, are collected. Every fraction, 70 through 93, is assayed at a dilution of 1:300. The bio-activity is found in fractions 73 through 82, reaching a maximum in fractions 77 and 78. Fractions 75 through 80 are freeze-dried to obtain 90 mg. of antibiotic with an average potecny of 10,000 units/mg.

The 90 mg. of freeze-dried solid is taken up into 4 ml. of 0.01M potassium phosphate buffer, pH 7. This solution, containing 596 hydroxylamine-extinguishable optical density units (this measure of the thienamycin content being described at the end of this Example) is applied on a 1.7 cm. diameter column packed with 90 ml. prewashed XAD-2 and equilibrated prior to use with 180 ml. of 0.01M potassium phosphate buffer, pH 7, at 5° C. The XAD-2 is washed prior to use successively with (1) 5 volumes of 1N NaOH followed by deionized H$_2$O until effluent is neutral; (2) 5 volumes 1N HCl followed by deionized H$_2$O until the effluent is neutral; (3) 5 volumes each of methanol, acetone, 0.001M EDTA tetrasodium, and finally distilled H$_2$O. Vacuum is applied to all solvents before use.

After the sample is applied on the column it is followed by two, 2 ml. portions of the phosphate buffer. The column is developed at 5° C. with the buffer at a flow rate of 2 ml./min. Four ml. fractions of eluate are collected. Fractions obtained after 100 ml. of eluate has been collected and ending with 253 ml. are combined and concentrated on a rotary evaporator under vacuum and below 10° C. to a volume of 6 ml.

This solution containing 436 hydroxylamine-extinguishable optical density units is applied on a 1.7 cm. diameter column packed with 90 ml. XAD-2 prewashed as above and equilibrated at 5° C. with distilled water. The sample is followed by two, 2 ml. portions of distilled water. The column is developed with distilled water at the rate of 2 ml./min. Four ml. fractions of eluate are collected. Fractions obtained after 100 ml. of eluate has been collected and ending with 151 ml. are pooled and concentrated on a rotary evaporator to a volume of 2.73 ml. and the solution lyophilized to yield 6.49 mg. of thienamycin. Fractions obtained between 152 ml. and 345 ml. are pooled and concentrated on a rotary evaporator to a volume of 3.34 ml. and lyophilized to yield 11.53 mg. of antibiotic. These fractions contain a total of 369 hydroxylamine-extinguishable optical density units. This represents a 3.1 fold purification over the material applied to the first XAD-2 column and yields a calculated potency of 31,000 units/mg. Spectrophotometric analysis of a sample of this product shows an $E_{1cm.}^{1\%} = 253$ when measured in phosphate buffer, pH 7, at 297 nm.

Hydroxylamine-Extinguishable Absorbance

The proportion of absorbance measured at 297 nm which can be attributed to the antibiotic content in impure samples is determined by the selective extinction of this absorbance (with concommitant inactivation of antibiotic activity) upon reaction with dilute hydroxylamine.

Samples are prepared in 0.01M potassium phosphate buffer at pH 7.0 to have an initial $A_{297}$ between 0.05 and 2.0. Freshly prepared, neutral hydroxylamine ($NH_2OH.HCl$ plus NaOH to a final pH of 7) is added to a final concentration of 10 mM., and reaction is allowed to progress at room temperature for at least 30 min. The resulting $A_{297}$ when substracted from the initial reading (after correction for dilution by added reagent) yields the hydroxylamine-extinguishable absorbance. Solutions of pure thienamycin show a hydroxylamine-extinguishable absorbance of 94.5%.

EXAMPLE 7

A 10 g. portion of the 99 g. freeze-dried solids obtained by the Dowex 1 × 2 purification in Example 6 is taken up in 0.1M 2,6-lutidien acetate buffer, pH 6.3. The solution, 125 ml., readjusted to pH 6.3 with acetic acid, is applied to a 7.6 × 142 cm. column of Dowex 50 × 8 in the 2,6-lutidine cycle, which had previously been equilibrated with buffer. The column is developed with 0.1M buffer at 35 ml./min. A 3.6 l. fore-cut is collected followed by 200 fractions of 20 ml. each. Every fourth fraction 6 through 194 is assayed at a dilution of 1:200. The bioactivity is contained in fractions 18 through 178, reaching a maximum in fractions 62 through 82. Fractions 42 through 102 are combined and 640 ml. of deionized water added to give 1920 ml. The pooled, diluted, solution containing 63% of the bio-activity applied on the Dowex 50 × 8 column, is freeze-dried.

The freeze-dried solids are dissolved in 0.1M 2,6-lutidine acetate, pH 7.0 buffer. The solution, 25 ml., is applied to a 5 × 112 cm. column of Bio-Gel P-2 (200–400 mesh), which had previously been equilibrated with 0.1M buffer. The gel is then developed with the same buffer at 10 ml./min.

The effluent stream is monitored with a Meccomatic recording differential refractometer. The development is continued until 125 fractions, 20 ml. each, are collected. Every fraction, 70 through 89, is assayed at a dilution of 1:300. The bio-activity is found in fractions 72 through 81, reaching a maximum in fraction 77. Fractions 75 through 79 are freeze-dried to obtain 100.5 mg. of antibiotic with a potency of 8,320 units/mg.

The 100.5 mg. of freeze-dried solid is taken up into 4 ml. of 0.01M potassium phosphate buffer, pH 7. This solution, containing 692 hydroxylamine-extinguishable optical units is applied on a 1.7 cm. diameter column packed with 90 ml. prewashed XAD-2 and equilibrated prior to use with 180 ml. of 0.01M potassium phosphate buffer, pH 7, at 5° C. The XAD-2 is washed prior to use successively with (1) 5 volumes of 1N NaOH followed by deionized $H_2O$ until effluent is neutral; (2) 5 volumes in 1N HCl followed by deionized $H_2O$ until the effluent is neutral; (3) 5 volumes each of methanol, acetone, 0.001M EDTA tetrasodium, and finally distilled $H_2O$. Vacuum is applied to all solvents before use.

After the sample is applied on the column it is followed by two, 2 ml. portions of the phosphate buffer. The column is developed at 5° C. with the buffer at a flow rate of 2 ml./min. Four ml. fractions of eluate are collected. Fractions obtained after 109 ml. of eluate has been collected and ending with the 309th ml. are combined. To this combined eluate is added the 11.53 mg. sample of XAD-2 purified antibiotic obtained in Example 6 comprising 186 hydroxylamine-extinguishable optical density units. The combined eluate together with the added antibiotic is concentrated in vacuo on a rotary evaporator at a temperature below 10° C. to a volume of 7 ml.

This solution, containing 720 hydroxylamine-extinguishable optical density units is applied on a 1.7 cm. diameter column packed with 90 ml. XAD-2 prewashed as above and equilibrated at 5° C. prior to use with distilled water. The sample is followed by two, 2 ml. portions of distilled water. The column is developed with distilled water at the rate of 2 ml./min. Four ml. fractions of eluate are collected. Fractions obtained after 109 ml. of eluate have been collected and ending with the 301st ml. are pooled and concentrated on a rotary evaporator to a volume of 10.3 ml. This solution, containing 589 hydroxylamine-extinguishable optical density units, is lyophilized to yield 23.6 mg. of antibiotic with a calculated potency of 30,140 units/mg.

The antibiotic thus prepared is a white, amorphous solid with a fibrous consistency, a sample of which on exposure in a glass capillary tube to temperatures elevated at a rate of 3C° per minute, underwent decomposition without the intervention of a liquid phase in the following stages: softening occurred at 130° to 140° C. with a contraction in volume of the solid continuing until 170° to 174° C. in which range the material yellowed; sintering and a progressive intensification of color to reddish-brown being observed in the range 180° to 200° C. and finally carbonisation and residual traces of solid being found at 205° C.

A further sample of this material on spectrophotometric analysis shows an absorbance peak at 296.5 nm with an $E_{1cm.}^{1\%} = 268.2$. Elemental analysis yields the following results: (1) a 5.67% weight loss upon drying at room temperature for 4 hours under vacuum, and (2) the composition 47.68% carbon, 6.22% hydrogen, 11.48% nitrogen. These results are consistent with the empirical formula $C_{11}H_{16}N_2O_4S \cdot (NH_3)_{0.28}$, the calculated elemental composition corresponding to this empirical formula being C=47.68%, H=6.13%, N=11.52%, S=11.57% and O=23.1%. Polarimetric analysis of a 1 mg./ml. solution of this sample in 10 mM potassium phosphate buffer showed a specific optical rotation $[\alpha]_D^{27°C.} + 80$. The infrared spectrum (FIG. 1) of a nujol mull of this sample revealed characteristic absorption peaks at 1765 $cm.^{-1}$, 1650–1550 $cm.^{-1}$, 2800–2500 $cm.^{-1}$, and 3500–3100 $cm.^{-1}$. An NMR spectrum at 100 MHz of a sample of this product dissolved in $D_2O$ revealed a doublet at $\alpha 1.275$, a pair of doublets at $\alpha 3.39$ and multiplets at $\alpha 3.15$ and $\alpha 4.20$, these peaks being characteristic of thienamycin.

Compositions containing the antibiotic may be administered in several unit dosage forms as, for example, in solid or liquid orally ingestible dosage form. The compositions per unit dosage, whether liquid or solid may contain from 0.1% to 99% of active material, the preferred range being from about 10 to 60%. The composition will generally contain from about 25 mg. to about 1000 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Representative formulations can be prepared by the following procedures:

| Capsules | Per Capsule |
|---|---|
| Thienamycin | 400 mg. |
| Lactose, U.S.P., a sufficient quantity | |
| (Fill No. 0 Capsules, approx. 475 mg. each) | |

In the above example the active compound and the diluent are mixed to produce a uniform blend, which is then filled into No. 0 hard gelatin capsules, by hand or on a suitable machine, as required. The mixing and filling is preferably done in an area having a relative humidity less than 40%.

| Tablets | Per Tablet |
|---|---|
| Thienamycin | 330. mg. |
| Calcium phosphate | 192. mg. |
| Lactose, U.S.P. | 190. mg. |
| Cornstarch | 80. mg. |
| Magnesium stearate | 8. mg. |
| | 800. mg. |

In the above example, the active component is blended with the calcium phosphate, lactose and about half of the cornstarch. The mixture is granulated with a 15% cornstarch paste and rough-screened and screened again through No. 16 screens. The balance of the cornstarch and the magnesium stearate is added and the mixture is compressed into tablets, approximately ½ inch in diameter, each weighing 800 mg.

Alternatively, the active component is blended with the calcium phosphate, lactose and one-half the cornstarch. The mixture is "slugged" on a heavy duty press to produce compacted tablet-like masses. These are broken down to a No. 16 mesh granule. The balance of the cornstarch and the magnesium stearate are added and the mixture is compressed into tablets approximately ½ inch in diameter, each weighing 800 mg.

| Lyo Form (For Injection) | Per Vial |
|---|---|
| Thienamycin | 25 mg. |
| Water-for-Injection, U.S.P. to make | 5 ml. |

In the above example the active component is dissolved in sufficient water-for-injection in the ratio shown. The solution is filtered through Selas candles or Millipore membrane filters to sterilize. The solution is subdivided into sterile vials. The vials and contents are frozen, and the water is aseptically removed by lyophilization. The vials containing the sterile dry solid are aseptically sealed.

To restore for parenteral administration, 5 ml. of sterile water-for-injection is added to the contents of a vial.

| Oral Liquid Forms | Per 1000 ml. |
|---|---|
| Thienamycin | 1.0 gm. |
| Sucrose | 600.0 gm. |
| Glucose | 250.0 gm. |
| Sodium Benzoate | 1.0 gm. |
| Concentrated Orange Oil | 0.2 ml. |
| Purified water U.S.P. to make | 1000.0 ml |

The sucrose and glucose are dissolved in about 400 ml. of water using heat to aid solution. This solution is cooled and sodium benzoate, followed by the concentrated orange oil added. The solution is brought to about 900 ml. volume with water and the antibiotic is added. The solution is clarified by filtration through a coarse filter.

What is claimed is:

1. An antibacterial composition comprising an antibacterial effective amount of the compound:

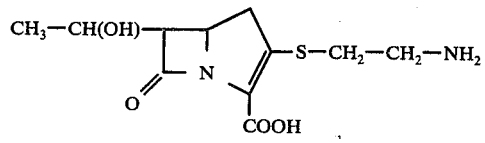

and a non-toxic pharmaceutically acceptable carrier therefore.

* * * * *